United States Patent
Chuang et al.

(10) Patent No.: US 12,065,530 B2
(45) Date of Patent: *Aug. 20, 2024

(54) OXAZOLIDINEDIONE-TERMINATED PREPOLYMER

(71) Applicant: Huntsman International LLC, The Woodlands, TX (US)

(72) Inventors: Ya-Mi Chuang, Lanaken (BE); Giulio Marini, Leuven (BE); Christopher Phanopoulos, Tervuren (BE)

(73) Assignee: HUNTSMAN INTERNATIONAL LLC, The Woodlands, TX (US)

( * ) Notice: Subject to any disclaimer, the term of this patent is extended or adjusted under 35 U.S.C. 154(b) by 714 days.

This patent is subject to a terminal disclaimer.

(21) Appl. No.: 17/273,193

(22) PCT Filed: Sep. 5, 2019

(86) PCT No.: PCT/EP2019/073681
§ 371 (c)(1),
(2) Date: Mar. 3, 2021

(87) PCT Pub. No.: WO2020/053061
PCT Pub. Date: Mar. 19, 2020

(65) Prior Publication Data
US 2021/0324132 A1 Oct. 21, 2021

(30) Foreign Application Priority Data

Sep. 10, 2018 (EP) .................................. 18193387

(51) Int. Cl.
| | |
|---|---|
| C08G 18/12 | (2006.01) |
| C07D 263/44 | (2006.01) |
| C08G 18/20 | (2006.01) |
| C08G 18/28 | (2006.01) |
| C08G 18/32 | (2006.01) |
| C08G 18/48 | (2006.01) |
| C08G 18/76 | (2006.01) |

(52) U.S. Cl.
CPC .......... C08G 18/12 (2013.01); C07D 263/44 (2013.01); C08G 18/2081 (2013.01); C08G 18/284 (2013.01); C08G 18/325 (2013.01); C08G 18/4825 (2013.01); C08G 18/7671 (2013.01)

(58) Field of Classification Search
CPC ...... C08G 18/32; C08G 18/12; C08G 18/325; C08G 18/2081; C08G 18/284; C08G 18/7671
See application file for complete search history.

(56) References Cited

U.S. PATENT DOCUMENTS

| | | | | |
|---|---|---|---|---|
| 4,220,787 A | * | 9/1980 | Scholz | C07D 263/44 548/226 |
| 4,233,450 A | * | 11/1980 | Scholz | C07D 263/44 528/226 |
| 6,177,523 B1 | | 1/2001 | Reich et al. | |
| 2008/0268261 A1 | * | 10/2008 | Schwoeppe | C09K 3/1021 428/432 |
| 2010/0151138 A1 | * | 6/2010 | Occhiello | C08G 18/10 427/407.1 |
| 2011/0059318 A1 | | 3/2011 | Harvey et al. | |
| 2013/0041100 A1 | | 2/2013 | Diamanti et al. | |
| 2014/0355225 A1 | | 12/2014 | Jordan, Jr. et al. | |
| 2016/0152762 A1 | * | 6/2016 | Nguyen-Kim | C08G 18/4854 514/406 |

FOREIGN PATENT DOCUMENTS

| | | | |
|---|---|---|---|
| CN | 108485622 A | 9/2018 | |
| EP | 1106634 A1 | 6/2001 | |
| WO | WO-2020070018 A1 * | 4/2020 | ............. C08G 18/10 |

OTHER PUBLICATIONS

International Search Report received in corresponding PCT Application PCT/EP2018/073681 completed Nov. 28. 2019 and mailed Dec. 9, 2019.
Written Opinion received in corresponding PCT Application PCT/EP2018/073681 mailed Dec. 9, 2019.

* cited by examiner

*Primary Examiner* — Michael L Leonard
(74) *Attorney, Agent, or Firm* — HUNTSMAN INTERNATIONAL LLC; Lewis Craft

(57) ABSTRACT

The present invention relates to a compound obtained by a process comprising the following steps: (i) Reacting at least one isocyanate containing compound, in stoichiometric excess, with at least one isocyanate-reactive compound having a number average molecular weight equal to or higher than 400, resulting in the formation of at least one prepolymer having soft blocks and hard blocks in its structure, which prepolymer contains unreacted isocyanate monomer, (ii) Reacting said at least one prepolymer with a hydroxyl-ester compound or a hydroxyl-acid compound with the formation of hydroxyl-ester terminated prepolymer or hydroxyl-acid terminated prepolymer, and Ring-closing said hydroxyl-ester terminated prepolymer or hydroxyl-acid terminated prepolymer; (iii) Formation of said compound made of oxazolidinedione-terminated prepolymer and oxazolidinedione-terminated monomer, which is soluble in said oxazolidinedione-terminated prepolymer.

15 Claims, No Drawings

OXAZOLIDINEDIONE-TERMINATED PREPOLYMER

CROSS-REFERENCE TO RELATED APPLICATIONS

This application is the National Phase of International Application PCT/EP2019/073681 filed Sep. 5, 2019 which claims priority to European Application No. 18193387.0 filed Sep. 10, 2018. The noted applications are incorporated herein by reference.

The present invention relates to oxazolidinedione-terminated prepolymer, poly(urethane-amide) compound, and product comprising said poly(urethane-amide) compound.

Typically, isocyanate containing compounds are reacted with hydroxyl-ester compounds, such as ethyl lactate, in the presence of a catalyst, leading to the formation of urethane-ester compound, which can further be reacted with amine, under condensation reaction conditions. This will result in the formation of poly(urethane-amide) compounds.

Depending on the process/reaction conditions, poly(urethane-amide) compounds will have certain properties, which will define the end uses of the polymer obtained by the process.

Current processes providing amide containing polyurethane polymers are complex, expensive and uncertain regarding the applications of the final product.

For example, US 2013/0041100 A1 discloses such amide containing polyurethane polymers. In this document, pure 4,4'-diphenyl-methane diisocyanate (4,4'-MDI) is reacted with ethyl lactate, in the presence of a solvent and a catalyst. The reaction product is in solid state—urethane-ester compound. The latter is further reacted with amine, leading to the formation of poly(urethane-amide) compound.

Unfortunately, the reaction between 4,4'-MDI and ethyl lactate is accompanied by side reactions, which causes the formation of ethyl-urethane species. Side reactions should be avoided, since the functionality of the urethane-ester compound is reduced, which results in a lower degree of polymerisation.

For the aforementioned reasons, there is a need to provide a compound with higher functionality via a more efficient and simple process.

Unfortunately, as stated above, known urethane-ester compounds are obtained by complex, expensive and uncertain processes.

It is an object of the present invention to overcome the aforementioned drawbacks by providing a compound with higher functionality, which compound can be obtained by a cost-efficient, simpler and convenient process.

In this respect, the present invention provides a compound, made of oxazolidinedione-terminated prepolymer and oxazolidinedione-terminated monomer, being soluble in said oxazolidinedione-terminated prepolymer and obtained by a process comprising the following steps:
  (i) Reacting at least one isocyanate, in stoichiometric excess, with at least one isocyanate-reactive compound having a number average molecular weight higher than 400, resulting in the formation of at least one prepolymer having soft blocks and hard blocks in its structure, which prepolymer contains unreacted isocyanate monomer,
  (ii) Reacting said at least one prepolymer with a hydroxyl-ester compound or a hydroxyl-acid compound with the formation of hydroxyl-ester terminated prepolymer or hydroxyl-acid terminated prepolymer, and
  Ring-closing said hydroxyl-ester terminated prepolymer or hydroxyl-acid terminated prepolymer,
  (iii) Formation of said compound made of oxazolidinedione-terminated prepolymer and oxazolidinedione-terminated monomer, which is soluble in said oxazolidinedione-terminated prepolymer.

In the present invention, it has been unexpectedly discovered that forming a prepolymer by using at least one isocyanate-reactive compound having a number average molecular weight equal to or higher than 400, enables providing a prepolymer with appropriate properties. More precisely, the prepolymer of the present invention has soft blocks and hard blocks in its structure and contains unreacted isocyanate monomer.

When step (ii) is carried out, the unreacted isocyanate monomer contained in the prepolymer and the at least one prepolymer should react with the hydroxyl-ester compound or the hydroxyl-acid compound. This means that step (ii) is followed, after ring-closure, by the formation of a compound made of oxazolidinedione-terminated prepolymer and oxazolidinedione-terminated monomer—step (iii).

The compound obtained in step (iii) is then ready to be reacted with an amine, to provide poly(urethane-amide) compound having excellent mechanical properties, with the possibility of fine-tuning the properties of the polymer obtained by the process of the present invention.

Advantageously, said oxazolidinedione-terminated monomer is soluble in said oxazolidinedione-terminated prepolymer, in such a way that the obtained compound is in liquid state, which means that it is ready to be used, without the need to add any solvent.

The advantage of the compound of the present invention is linked to the fact that it is provided in liquid state. This is achieved thanks to the fact that the oxazolidinedione-terminated monomer is soluble in the oxazolidinedione-terminated prepolymer.

There is therefore no need to add further steps to dissolve the oxazolidinedione-terminated monomer.

Preferably, the aforementioned compound of the present invention is obtained by a process consisting of steps (i) to (iii).

It is therefore more convenient to process it, since it is a compound directly provided in liquid state, which enables formation of poly(urethane-amide) compound in a simple way, when mixed with amine, preferably provided in liquid state as well.

Preferably, said compound of the present invention has a non-Newtonian viscosity.

More preferably, wherein said at least one prepolymer has a non-Newtonian viscosity.

In a preferred embodiment of the present invention, said at least one isocyanate containing compound and said at least one isocyanate-reactive compound are reacted at a molar ratio (NCO:OH) ranging from 1.05 to 15, preferably 2 to 5.

According to a particular embodiment, said at least one prepolymer and said at least one hydroxyl-ester compound or said hydroxyl-acid compound are reacted at a molar ratio (NCO:OH) ranging from 0.5 to 1.2, preferably 0.5 to 1.

According to a particular feature of the invention, said at least one prepolymer has an NCO value ranging from 0.8 to 10%, before performing step (ii).

According to a preferred embodiment, step (ii) is performed at a first temperature, preferably ranging from 50° C. to 100° C., preferably from 60° C. to 90° C., more preferably from 60° C. to 80° C., resulting in the formation of a hydroxyl-ester terminated prepolymer or a hydroxyl-acid terminated prepolymer.

In particular, step (ii) consists in reacting the at least one prepolymer with a hydroxyl-ester compound or hydroxyl-acid compound in order to form an intermediate product, such as an ethyl-lactate terminated prepolymer. This step is advantageously catalyst free.

Advantageously, step (ii) is carried out, at said first temperature, preferably in a catalyst free condition.

Without being bound to the theory, it is believed that, when step (ii) consists in reacting the at least one prepolymer with a hydroxyl-ester compound, such as ethyl lactate, or hydroxyl-acid compound, the release of ethanol can be avoided, and this increases the degree of polymerization by reducing the formation of side-groups.

Preferably, step (ii) also comprises a ring-closure step by processing said hydroxyl-ester terminated prepolymer or said hydroxyl-acid terminated prepolymer, preferably in the presence of at least one catalyst, at a second temperature, which can be higher than said first temperature, resulting in the formation of oxazolidinedione-terminated prepolymer and oxazolidinedione-terminated monomer, as referred in step (iii).

Alternatively, said second temperature can be equal or lower than said first temperature.

Advantageously, the second temperature ranges from 80° C. to 120° C., preferably from 90° C. to 110° C.

The ring-closure step is preferably performed after formation of said intermediate product—hydroxyl-ester terminated prepolymer or said hydroxyl-acid terminated prepolymer—and, more preferably, in the presence of a catalyst.

More specifically, the hydroxyl-ester terminated prepolymer or said hydroxyl-acid terminated prepolymer also contains hydroxyl-ester terminated monomer or hydroxyl-acid terminated monomer, even if not specifically indicated throughout the application.

In an advantageous embodiment, it has been observed that processing the at least one prepolymer with hydroxyl-ester compound or hydroxyl-acid compound, preferably at a first temperature and the obtained intermediate product, preferably at a second temperature enables providing the compound (i.e. oxazolidinedione-terminated prepolymer, wherein oxazolidinedione-terminated monomer is soluble) of the present invention with improved properties, by using cost-efficient and simpler process.

According to a preferred embodiment of the present invention, step (ii) of the present invention consists in the following steps:
  reacting the at least one prepolymer with a hydroxyl-ester compound or hydroxyl-acid compound in order to form an intermediate product, such as an ethyl-lactate terminated prepolymer (preferably, in a catalyst free condition), and
  ring-closing by processing said hydroxyl-ester terminated prepolymer or said hydroxyl-acid terminated prepolymer, preferably in the presence of at least one catalyst, more preferably at a second temperature, which can be higher than said first temperature, resulting in the formation of oxazolidinedione-terminated prepolymer and oxazolidinedione-terminated monomer, which is soluble in said oxazolidinedione-terminated prepolymer—step (iii).

In an advantageous embodiment of the present invention, said catalyst is selected from the group consisting of 1,4-Diazabicyclo[2.2.2]octane (DABCO), 1,8-Diazabicyclo (5.4.0)undec-7-ene (DBU), Triazabicyclodecene (TBD), triethylamine, and potassium t-butanoate.

Preferably, said hydroxyl-ester compound is selected from the group consisting of alpha-hydroxy ester compounds, hydroxyl containing esters derived from fatty acids, natural oils containing hydroxyl groups, and combinations thereof.

In some embodiments, the hydroxyl-ester is an alpha-hydroxyl-ester compound, preferably a lactate, more preferably a lactate selected from the group comprising ethyl lactate, butyl lactate, iso-butyl lactate, propyl lactate, and methyl lactate, yet more preferably said lactate is ethyl lactate.

Preferably, the hydroxyl acid compounds include, but are not limited to alpha-hydroxy acids. Exemplary hydroxyl acids include, but are not limited to, glycolic acid, 2-hydroxypropionic acid, 2,3-dihydroxypropanoic acid (glyceric acid), 2-hydroxybutyric acid, hydroxybutanedioic acid (malic acid), 2,3-dihyroxybutanedioic acid (tartaric acid), dihydroxypentanoic acid, 2-hydroxypentanedioic acid (alpha-hydroxylglutaric acid); 2-hydroxyhexanic acid. The hydroxyl acid compound can preferably have four or more carbon atoms, citric acid, malic acid, tartaric acid, and the like can be given. As the hydroxyl acid, a citric acid, a tartaric acid and a malic acid may be exemplified.

In the context of the present invention, "hydroxyl acid compound" has preferably at least one hydroxyl group and at least one acidic-functional group, where said hydroxyl group is in a position, with respect to said at least one acidic-functional group.

In a particular aspect of the invention, said at least one prepolymer has a hard block content ranging from 20 to 35 wt. %, based on the total weight of said at least one prepolymer.

In a more particular aspect of the invention, said compound of the invention has a hard block content ranging from 30 to 55 wt. %, based on the total weight of said compound.

Other embodiments of the compound of the present invention are mentioned in the annexed claims.

The present invention also relates to a poly(urethane-amide) compound obtained by reacting a compound (i.e. oxazolidinedione-terminated prepolymer, wherein oxazolidinedione-terminated monomer is soluble) according to the present invention, with at least one amine having a functionality of at least 1.8, preferably of at least 2.

Preferably, the hard block content of the poly(urethane-amide) is at least 5%, preferably at least 10%, preferably at least 15%, preferably at least 20%, preferably at least 25%; preferably the hardblock content is ranging from 5% to 85%.

Other embodiments of the poly(urethane-amide) compound of the present invention are mentioned in the annexed claims.

The present invention further concerns a product comprising poly(urethane-amide) compound according to the present invention.

Other embodiments of the product comprising poly(urethane-amide) compound are mentioned in the annexed claims.

The present invention provides a poly(urethane-amide) compound that can be used for the preparation of adhesives, coatings, elastomers, and foams.

According to the invention, step (ii) relates to the reaction between said at least one prepolymer of the invention and hydroxyl-ester compound or hydroxyl-acid compound resulting in the formation of an intermediate product. This intermediate product is defined in the present application as hydroxyl-ester terminated prepolymer or as hydroxyl-acid terminated prepolymer, as exemplified in scheme B.

In the context of the present invention, the "ring-closure step" or "ring-closing" expressions should be understood as a process step, which is applied on the intermediate product obtained in step (ii). The intermediate product is hydroxyl-ester terminated prepolymer or hydroxyl-acid terminated prepolymer, as explained above.

The "ring-closure step" enables forming a compound (as exemplified in scheme C), which is made of oxazolidin-edione-terminated prepolymer and oxazolidinedione-terminated monomer, which is soluble in said oxazolidinedione-terminated prepolymer. The final product comprises a 5-membered ring structure, as exemplified in scheme C.

In this context, the compound of the present invention is the final 5-membered-ring product obtained after applying the ring-closure step—referred in the application as step (iii).

Suitable prepolymers are known in the art and commercially available. They are, preferably, the reaction product of an isocyanate containing compound with an isocyanate-reactive compound. Such prepolymers are generally prepared by reacting, in molar excess, of polymeric or pure aromatic isocyanate monomers with one or more polyol(s) using reactive conditions known in the art. The polyols may include aminated polyols, imine or enamine modified polyols, polyether polyols, polyester polyols, polyamines, such as alkanol amines, as well as diols and triols.

Suitable isocyanate containing compound for use in the preparation of the prepolymer may be aromatic, or aralipahtic organic isocyanates. Suitable aromatic isocyanates include also polyisocyanates.

Suitable polyisocyanates comprise polyisocyanates of the type Ra-(NCO)x, with x being at least 2 and Ra being an aromatic such as diphenylmethane, or toluene, or a similar polyisocyanate.

Non-limiting examples of suitable aromatic polyisocyanate monomers that can be used in the present invention can be any polyisocyanate compound or mixture of polyisocyanate compounds, preferably wherein said compound(s) comprise(s) preferably at least two isocyanate groups.

Non-limiting examples of suitable aromatic polyisocyanate monomers include diisocyanates, particularly aromatic diisocyanates, and isocyanates of higher functionality. Non-limiting examples of aromatic polyisocyanate monomers which may be used in the present invention include aromatic isocyanate monomers such as diphenylmethane diisocyanate (MDI) in the form of its 2,4'-, 2,2'- and 4,4'-isomers and mixtures thereof (also referred to as pure MDI), the mixtures of diphenylmethane diisocyanates (MDI) and oligomers thereof (known in the art as "crude" or polymeric MDI), m- and p-phenylene diisocyanate, tolylene-2,4- and tolylene-2,6-diisocyanate (also known as toluene diisocyanate, and referred to as TDI, such as 2,4 TDI and 2,6 TDI) in any suitable isomer mixture, chlorophenylene-2,4-diisocyanate, naphthylene-1,5-diisocyanate, diphenylene-4,4'-diisocyanate, 4,4'-diisocyanate-3,3'-dimethyl-diphenyl, 3-methyl-diphenylmethane-4,4'-diisocyanate and diphenyl ether diisocyanate; tetramethylxylene diisocyanate (TMXDI), and tolidine diisocyanate (TODI); any suitable mixture of these polyisocyanates, and any suitable mixture of one or more of these polyisocyanates with MDI in the form of its 2,4'-, 2,2'- and 4,4'-isomers and mixtures thereof (also referred to as pure MDI), the mixtures of diphenylmethane diisocyanates (MDI) and oligomers thereof (known in the art as "crude" or polymeric MDI), and reaction products of polyisocyanates (e.g. polyisocyanates as set out above, and preferably MDI-based polyisocyanates). Preferably diphenylmethane diisocyanate (MDI) or toluene diisocyanates (TDI)-type isocyanates are used.

In some embodiments, said aromatic isocyanate monomer comprises a polymeric methylene diphenyl diisocyanate. The polymeric methylene diphenyl diisocyanate can comprise any mixture of pure MDI (2,4'-, 2,2'- and 4,4'-methylene diphenyl diisocyanate) and higher homologues of formula (X):

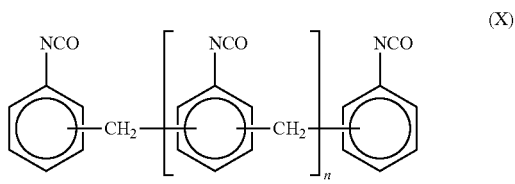

(X)

wherein n is an integer which can be from 1 to 10 or higher, preferably does not exclude branched version thereof.

Preferably, the aromatic isocyanate monomer comprises diphenylmethane diisocyanate (MDI), polymeric forms thereof, and/or variants thereof (such as uretonimine-modified MDI).

The isocyanate-reactive compound may be a component containing isocyanate-reactive groups. As used herein, the term "isocyanate-reactive groups" refers to chemical groups susceptible to electrophilic attack by an isocyanate group.

Non-limiting examples of said groups can be OH. In some embodiments, said isocyanate-reactive compound comprises at least one OH group. Examples of suitable isocyanate-reactive compounds containing isocyanate-reactive OH atoms include polyols such as glycols or even relatively high molecular weight polyether polyols and polyester polyols, carboxylic acids such as polybasic acids.

In some preferred embodiments, the at least one isocyanate-reactive compound is selected from the group comprising hydroxyl terminated polyether (polyether polyols); polyols such as glycols; hydroxyl terminated polyester (polyester polyols); and mixtures thereof, all of which are well known to those skilled in the art.

Suitable hydroxyl terminated polyethers are preferably polyether polyols derived from a diol or polyol having a total of from 2 to 15 carbon atoms, preferably an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide. Primary hydroxyl groups resulting from ethylene oxide are more reactive than secondary hydroxyl groups and are thus preferred. Useful commercial polyether polyols include poly(ethylene glycol) comprising ethylene oxide reacted with ethylene glycol, poly(propylene glycol) comprising propylene oxide reacted with propylene glycol, poly(tetramethylglycol) (PTMG) comprising water reacted with tetrahydrofuran (THF). Polyether polyols further include polyamide adducts of an alkylene oxide and can include, for example, ethylenediamine adduct comprising the reaction product of ethylenediamine and propylene oxide, diethylenetriamine adduct comprising the reaction product of diethylenetriamine with propylene oxide, and similar polyamide type polyether polyols. Copolyethers can also be utilized in the current invention. Typical copoethers include the reaction product of glycerol and ethylene oxide or glycerol and propylene oxide.

The isocyanate-reactive compound of the present invention has a number average molecular weight equal to or higher than 400 g/mol, preferably equal to or higher than 500 g/mol. Preferably, polyols have a number average molecular weight equal to or higher than 400 g/mol, preferably equal to or higher than 500 g/mol.

For isocyanate-reactive compound having a number average molecular weight equal to or higher than 400 g/mol, more preferably equal to or higher than 500, the various polyethers can have a molecular weight (MW), of at least 500 to at most 20000 g/mol, desirably from at least 600 to at most 10000 g/mol, more preferably of at least 1000 to at most 8000 g/mol, even more preferably from at least 2000 to 6000 g/mol, and most preferably of at least 2000 to at most 4000 g/mol.

For isocyanate-reactive compound having a number average molecular weight of 400 g/mol or more, preferably of 500 g/mol or more, suitable hydroxyl terminated polyesters (polyester polyols), can be generally a polyester having a molecular weight (MW) of at least 500 to at most 20000 g/mol, desirably from at least 600 to at most 10000 g/mol, more preferably of at least 1000 to at most 8000 g/mol, even more preferably from at least 2000 to 6000 g/mol, and most preferably of at least 2000 to at most 4000 g/mol.

The molecular weight is determined by assay of terminal functional groups and is related to the number average molecular weight.

The hydroxyl terminated polyester can be produced by (1) an esterification reaction of one or more glycols with one or more dicarboxylic acids or anhydrides, or (2) by transesterification reaction, i.e. the reaction of one or more glycols with esters of dicarboxylic acids. Mole ratios generally in excess of more than one mole of glycol to acid are preferred so as to obtain linear chains having a preponderance of terminal hydroxyl groups. Suitable polyesters also include various lactones such as polycaprolactone typically made from caprolactone and a bifunctional initiator such as diethylene glycol. The dicarboxylic acids of the desired polyester can be aliphatic, cycloaliphatic, aromatic, or combinations thereof. Suitable dicarboxylic acids which can be used alone or in mixtures generally have a total of from 4 to 15 carbon atoms and include: succinic, glutaric, adipic, pimelic, suberic, azelaic, sebacic, dodecanedioic, isophthalic, terephthalic, cyclohexane dicarboxylic, and the like. Anhydrides of the above dicarboxylic acids such as phthalic anhydride, tetrahydrophthalic anhydride, or the like, can also be used. Adipic acid is the preferred acid. The glycols which are reacted to form a desirable polyester intermediate can be aliphatic, aromatic, or combinations thereof, and have a total of from 2 to 12 carbon atoms, and include ethylene glycol, 1,2-propanediol, 1,3-propanediol, 1,3-butanediol, 1,4-butanediol, 1,5-pentanediol, 1,6-hexanediol, 2,2-dimethyl-1,3-propanediol, 1,4-cyclohexanedimethanol, decamethylene glycol, dodecamethylene glycol, and the like. 1,4-Butanediol is the preferred glycol.

In some embodiments, the isocyanate-reactive compound can be reacted with at least one isocyanate, along with extender glycol. Non-limiting examples of suitable extender glycols (i.e., chain extenders) include lower aliphatic or short chain glycols having from about 2 to about 10 carbon atoms and include, for instance, ethylene glycol, diethylene glycol, propylene glycol, dipropylene glycol, 1,4-butanediol, 1,6-hexanediol, 1,3-butanediol, 1,5-pentanediol, 1,4-cyclohexanedimethanol, hydroquinone di(hydroxyethyl)ether, neopentylglycol, and the like.

Non-limiting examples of suitable catalyst for the ring-closure reaction include 1,4-Diazabicyclo[2.2.2]octane (DABCO), 1,8-Diazabicyclo(5.4.0)undec-7-ene (DBU), Triazabicyclodecene (TBD), triethylamine, and potassium t-butanoate.

Suitable catalysts that may be used in the present invention, include without limitation, tertiary amines, tin-containing compounds, any standard urethane catalyst known in the polyurethane formation art such as triethylene diamine (TEDA), dibutyl tin dilaurate (DBTDL), titanium or zirconium containing compounds (e.g., TYZOR available from DuPont), or combinations thereof. Preferably, the catalyst is present in an amount of at least 10 ppm, preferably at least 0.01% by weight, preferably at least 0.05% by weight, with % by weight based on the total weight of the prepolymer.

In a preferred embodiment, steps (i) and (ii) are performed in a solvent free condition.

Suitable amine compounds that may be used in the present invention include, without limitation, di-functional amines, polyfunctional amines, mixtures of amines or combinations thereof. For example, primary amines, secondary amines, or combinations thereof may be used as the amine compound in the present invention. Preferably primary amines are used. Most preferably primary amine unhindered on the carbon in alpha of the amine. Examples of such amines include, without limitation, those selected from the group consisting of 1,2-ethanediamine, N,N'-bis(3-aminopropyl)methylamine, N,N'-dimethylethylene diamine, neopentanediamine, 4,4'-diaminodiphenyl methane and 2-methylpentamethylenediamine (such as DYTEK A available from Invista, Wilmington, Del., U.S.A.). Additionally, polyetheramines (such as JEFFAMINE polyetheramines available from the Huntsman Corporation, The Woodlands, Tex., U.S.A.), (such as ELASTAMINE HT1100, ECA-29, EDR 148) may be used in the invention, and combination thereof.

The molar ratio between the oxazolidinedione groups of the compound of the present invention (i.e. oxazolidinedione-terminated prepolymer, wherein oxazolidinedione-terminated monomer is soluble) and primary amine $NH_2$ can range from 0.8-1.10:1.0-1.10, preferably 0.9-1.05:1.0-1.05 and most preferably 0.95-1.05:1-1.05.

In some embodiments, the reaction with the amine can be conducted at a temperature ranging from 10° C. to 200° C., for example from 25° C. to 150° C., most preferably from 50° C. to 110° C.

If desired, a catalyst can be used to promote the formation of the poly(urethane-amide). Suitable catalysts that may be used include, without limitation, Lewis acids and bases, Bronstead acids and bases, or combinations thereof. Accordingly, suitable catalysts that may be used include, without limitation, DABCO, tin octoate, acetic acid, potassium tert-butoxide, or combinations thereof. While the reactive mixture used to form the poly(urethane-amide) compound described above could be catalyst free, in certain embodiments, a catalyst can be used. In these embodiments, the catalyst can be present in an amount ranging from 0.01 weight % to 10 weight %, such as 0.05 weight % to 1.5 weight %, based on the total weight of the ingredients used.

In some preferred embodiments, the poly(urethane-amide) is thermoplastic. A thermoplastic polymer is a type of plastic that changes properties when heat is applied, e.g., poly(urethane-amide) can melt below 100° C. The material can also be soluble in solvents. Non-limiting examples of such solvents include DMSO, DMF, Toluene, and Acetone.

The poly(urethane-amide) can be incorporated into a variety of compositions that can be used to make various end products. The present invention therefore also encompasses a product comprising the poly(urethane-amide) according to the invention.

Non-limiting list of suitable products comprises adhesives, sealants, coatings, elastomers, foams and the like.

In some embodiments, the product may be an adhesive. In some embodiments, the product may be an elastomer. In some other embodiments, the product may be a foam, such as one component foam. In yet other embodiments, the product may be a coating.

The present invention also relates to a process of manufacturing a compound, which process comprises the following steps:
a. Reacting at least one isocyanate, in stoichiometric excess, with at least one isocyanate-reactive compound having a number average molecular weight higher than 400, resulting in the formation of at least one prepolymer having soft blocks and hard blocks in its structure, which prepolymer contains unreacted isocyanate monomer,
b. Reacting said at least one prepolymer with a hydroxyl-ester compound or a hydroxyl-acid compound with the formation of hydroxyl-ester terminated prepolymer or hydroxyl-acid terminated prepolymer, Ring-closing the product obtained in step (b), and
c. Formation of said compound made of oxazolidinedione-terminated prepolymer and oxazolidinedione-terminated monomer, which is soluble in said oxazolidinedione-terminated prepolymer.

All the features mentioned for the compound (i.e. oxazolidinedione-terminated prepolymer, wherein oxazolidinedione-terminated monomer is soluble) obtained by the above-mentioned process are also applicable to the process of manufacturing the compound mentioned here above.

Moreover, and as explained here above, the obtained compound can be reacted with amine to provide poly(urethane-amide) compound. All technical features mentioned for the poly(urethane-amide) compound above apply mutatis mutandis.

In the context of the present invention, at least one isocyanate containing compound is reacted, in stoichiometric excess, with at least one isocyanate-reactive compound having a number average molecular weight equal to or higher than 400. This reaction step will result in the formation of at least one prepolymer having soft blocks and hard blocks in its structure and this prepolymer contains unreacted isocyanate monomer.

This means that a part of the isocyanate groups provided by the isocyanate containing polymer will react with the isocyanate reactive compound and a remaining part of the isocyanate groups provided by this isocyanate containing compound will not react with the isocyanate-reactive compound. This results in the formation of a prepolymer, which contains unreacted isocyanate monomer.

For example, the reaction between 4,4'-MDI, in stoichiometric excess, with a polyol will result in the formation of a prepolymer containing free-MDI, i.e., being the unreacted isocyanate monomer.

The prepolymer can preferably be reacted with ethyl lactate, preferably in a catalyst free condition.

Advantageously, it should be noted that the reaction with hydroxyl-ester compound (e.g., ethyl lactate) or hydroxyl-acid compound enables full end-capping of the isocyanate groups (final NCOv equal to 0%). This reaction is advantageously performed at a first temperature of about 70° C. and leads to the formation of ethyl lactate terminated prepolymer. The latter can further be reacted with a catalyst (ring-closure step), such as DABCO at a second temperature of about 100° C., resulting in the formation of the compound of the invention (i.e. oxazolidinedione-terminated prepolymer, wherein oxazolidinedione-terminated monomer is soluble) in liquid state, which compound is made of oxazolidinedione-terminated prepolymer and oxazolidinedione-terminated monomer, which is soluble in said oxazolidinedione-terminated prepolymer.

This compound in liquid state can further be reacted with amine to provide poly(urethane-amide) compound, having several end uses.

As indicated in the present invention, step (ii) comprises the ring-closure step, which is, preferably performed in the presence of a catalyst.

The term "hard block content of the prepolymer" refers to 100 times the ratio of the amount (in part by weight—pbw) of isocyanate+isocyanate-reactive compound having a number average molecular weight less than 400 over the amount (in pbw) of all isocyanates+all isocyanate-reactive compounds used in making the prepolymer.

The term "hard block content of the compound" refers to 100 times the ratio of the amount (in pbw) of isocyanate+isocyanate-reactive compound having an average molecular weight less than 400+oxazolidinedione reactive materials having molecular weight of less than 400, over the amount (in pbw) of all isocyanate+oxazolidinedione reactive materials+all isocyanate-reactive materials used.

The term "hard block content of the poly(urethane-amide) compound" refers to 100 times the ratio of the amount (in pbw) of isocyanate+oxazolidinedione ring opened material+isocyanate-reactive compound having molecular weight less than 400+oxazolidinedione reactive compound having molecular weight less than 400+amines having molecular weight less than 400, over the amount (in pbw) of all isocyanates+oxazolidinedione reactive materials+all isocyanate-reactive materials used+all amines used.

The term "soluble" used in the present invention should be understood as meaning that the oxazolidinedione-terminated monomer is visually soluble in the oxazolidinedione-terminated prepolymer. This results in one-single component, in liquid state. This solubility is visually observed.

As used herein, the term "isocyanate-containing compound" refers to a compound, which comprises at least one isocyanate group (—N=C=O), whereby the isocyanate group may be a terminating group. Preferably, the isocyanate group is a terminating group.

The isocyanate content (NCOv) (also referred to as percent NCO or NCO content) of prepolymers, given in weight %, was measured by conventional NCO titration following the standard ASTM D5155 method. In brief, isocyanate is reacted with an excess of di-n-butylamine to form ureas. The unreacted amine is then titrated with standard nitric acid to the color change of bromocresol green indicator or to a potentiometric endpoint. The percent NCO or NCO-value is defined as the percent by weight of NCO-groups present in the product.

In the context of the present invention, the expression "NCO value" corresponds to an isocyanate value, which is the weight percentage of reactive isocyanate (NCO) groups in an isocyanate containing compound, modified isocyanate or prepolymer and is determined using the following equation, where the molecular weight of the NCO group is 42:

$$\text{Isocyanate value} = \% \, NCO \text{ groups} = \frac{42 \times \text{Functionality}}{\text{Molecular weight}} \times 100.$$

13C-NMR spectroscopy was performed with a Bruker Avance III 500 MHz spectrometer by using a 5 mm probe at room temperature. The prepolymers were measured in acetone-d6, the compound of the present invention in DMSO-d6.

FT-IR analyses were performed with a Perkin Elmer 100 FT-IR spectrometer by ATR mode (16 scans, resolution 4 cm-1, 650 to 4000 cm-1 range).

The average molecular weight of the polyol and its distribution were analyzed via gel permeation chromatography (GPC) performed by dissolving the sample in THF (at 5 wt % concentration) and analyzed using a refractive index detector. Detection is based on retention time and is done by use of an UV detector. The Agilent G1310B instrument was equipped with 2×PL gel 5 μm columns (flow rate of 30 ml/min). Area % distribution of prepolymer peaks was given as a result. The obtained chromatogram was contrasted with a polystyrene standard calibration curve.

Young's modulus (kPa), Elongation at break (%), Stress at break (kPa) were measured according to ISO DIN53504. "Dog bone" specimen of the poly(urethane-amide) compound having a cross section of 4×2 mm were strained at 100 mm/min with an Instron device.

In the context of the present invention, viscosity can be measured via Rheometrics (a Brookfield R/S-CPS-P2 Rheometer fitted with C25-2 cone spindle at 350 Pa with a cone and plate geometry (CONE SST 20 mm×0.5)), using a shear rate of 100-300 rotation per minute, and a 250-450 micron truncation gap. The viscosity was measured at ambient temperature 20° C.

The examples described hereunder illustrate some embodiments of the present invention. Unless otherwise indicated, all parts and all percentages in the following examples, as well as throughout the specification, are parts by weight or percentages by weight respectively.

EXAMPLE 1

1. Preparation of the Prepolymer—Scheme A
250 g of 4,4'-MDI (1 mol, NCOv=33.6%) were weighed out in a round bottomed vessel equipped with mechanical stirrer, digital thermocouple, and water-cooled condenser. The temperature was raised to 70° C. under nitrogen flux. When the reaction temperature was reached, 1000 g of PPG (Mw=2000 g/mol, OHv=56 mg KOH) (0.5 mol) were added drop wise to the reaction vessel with a pressure equalized addition funnel under vigorous stirring, as illustrated in scheme A hereunder. The addition rate was controlled, in order to maintain a constant temperature inside the reactor. After the complete addition of PPG 2000, about 6 g of product were sampled to determine the NCO value of the prepolymer and to monitor the advancement of the reaction. When the desired NCOv was reached (=3.36±0.05%, determined via potentiometric titration as described above under methods), the prepolymer, which contains some unreacted MDI, was transferred into metal tins and stored under inert atmosphere at room temperature. Viscosity of the prepolymer is 29 Pa·s.

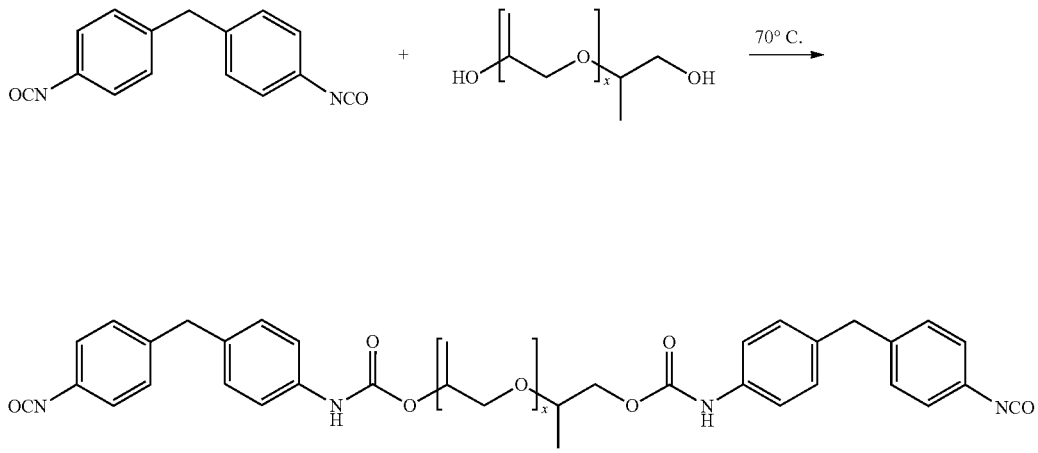

Scheme A

2. Reaction with Ethyl Lactate—Scheme B
250 g (0.1 mol) of the prepared prepolymer (NCOv equal to 3.36%±0.05%; 0.2 mol) of section 1 above, were weighted out in a round bottomed flask equipped with mechanical stirrer, digital thermocouple, and condenser. The temperature was raised to 70° C. under nitrogen blanket. When the reaction temperature was reached, an equivalent amount of ethyl lactate, 23.63 g (0.2 mol) was added drop-wise to the reaction vessel under mechanical stirring, as illustrated in scheme B hereunder. The viscosity of the mixture (ethyl lactate-terminated prepolymer, which contains ethyl lactate-terminated monomer, the latter not illustrated in scheme B below) was observed, in order to increase, together with the conversion of isocyanate groups to urethane groups. The reaction was followed via infrared spectroscopy analyzing a sample every 30 minutes and monitoring the disappearance of peak associated to the isocyanate groups at 2270 cm$^{-1}$. When the reaction was completed, the product was transferred into glass bottles and stored under inert atmosphere at ambient temperature.

Scheme B

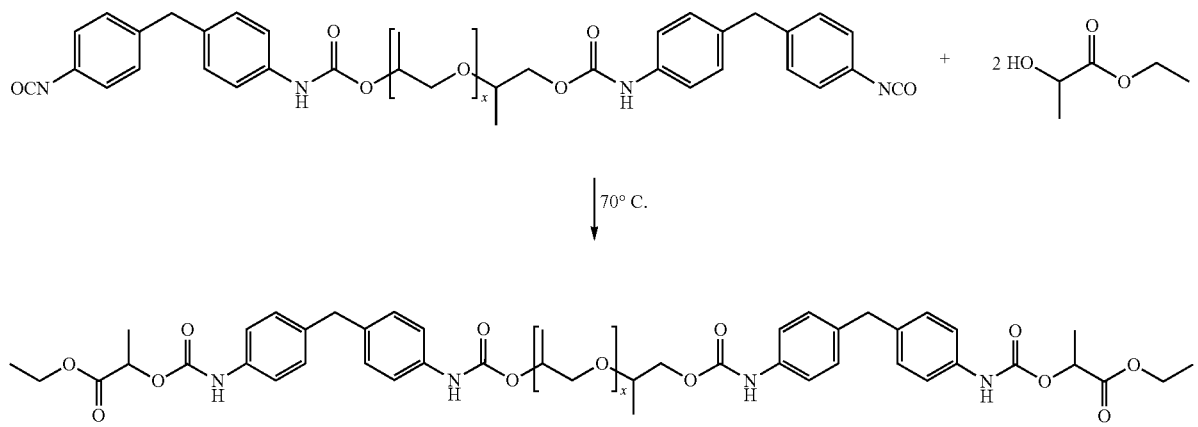

3. Synthesis of the Compound of the Present Invention—Ring Closure Step

Under the same condition as indicated for the reaction with ethyl lactate. The reaction product obtained in the above-mentioned step was poured into a 3-neck flask equipped with a Dean-Stark apparatus, thermocouple and mechanical stirrer. DABCO was added (0.05% by weight) and the temperature was raised to 100° C. The intramolecular reaction promotes the formation of ethanol that is distilled out of the reaction vessel. The reaction was monitored via FT-IR following the appearance of a new peak at 1816 cm$^{-1}$, associated to the stretching of the N—CO bonds in strained rings, the disappearance of the peak at 1726 cm$^{-1}$ of the esteric C=O in favour of an increased broad peak at 1742 cm-1. When the reaction was completed, the final product (compound of the invention) was collected in glass bottles without further purification and stored under nitrogen atmosphere.

The compound of the invention consists in oxazolidinedione-terminated prepolymer and oxazolidinedione-terminated monomer, where it has been visually observed that oxazolidinedione-terminated monomer is soluble in oxazolidinedione-terminated prepolymer. In this way, the final product is a compound in liquid state.

The oxazolidinedione-terminated prepolymers prepared contained no NCO groups.

EXAMPLE 2—SYNTHESIS OF POLY(URETHANE-AMIDE) COMPOUND

Polymerization of the product obtained in example 1, with amine (ECA-29), was carried out, as illustrated in scheme D hereunder.

Please note that other types of amine can be used, such as Jeffamine EDR 148; Elastamine HT1100; tris(2-aminoethyl)amine, including mixtures thereof.

50 g of the compound of example 1 were weighed out in a disposable glass bottle and heated up to 100° C. under nitrogen blanket. When the viscosity decreased, the compound was stirred with a mechanical mixer. When the reaction temperature was reached, an equimolar amount of primary amine(s) was added (the exact quantities are listed in Table 1). The mixture was homogenized for 20 seconds and transferred into a mould, pre-heated at 100° C., and allowed to cure for 1 hour.

Scheme C

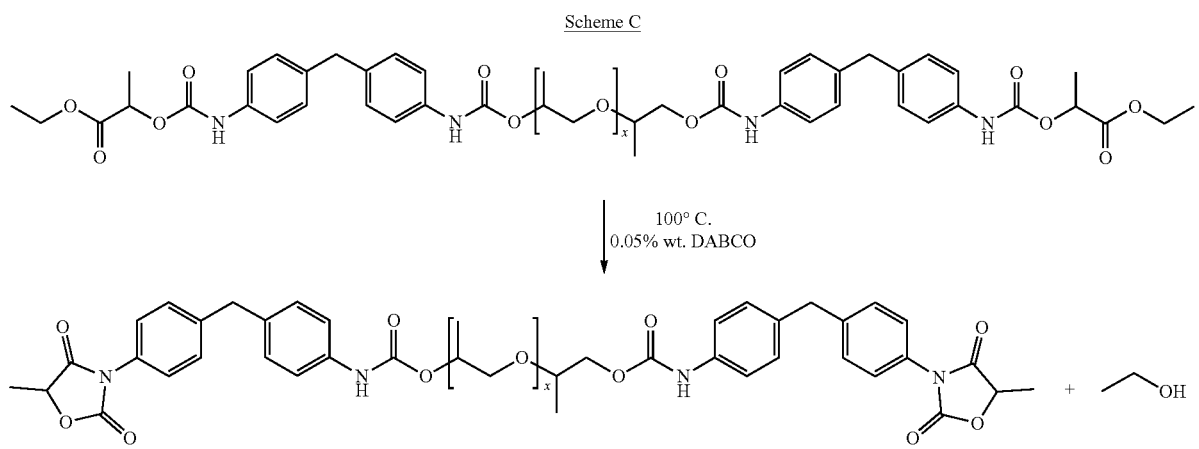

Scheme D

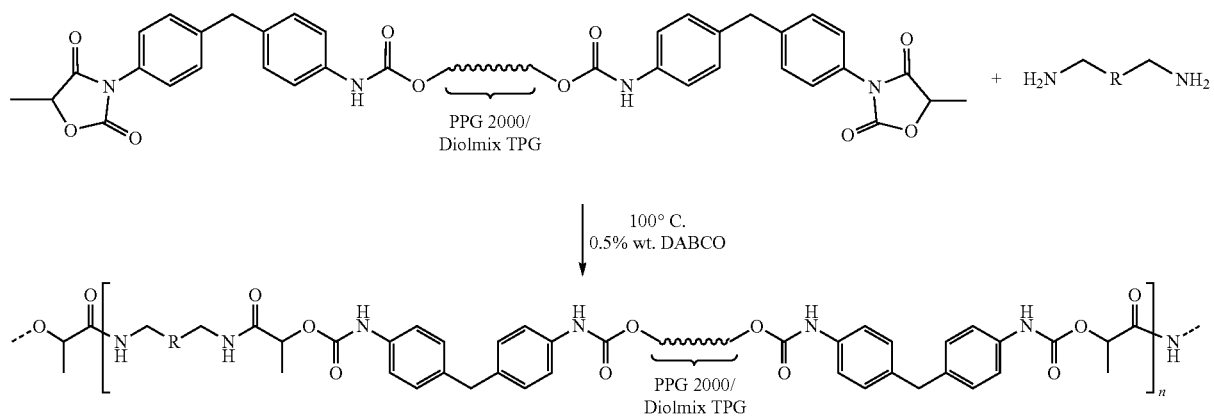

Mechanical Properties—Example 2

| Product | Hard block content in % (after cure) | Young's modulus (kPa) | Elongation at break (%) | Stress at break (kPa) |
|---|---|---|---|---|
| Poly(urethane-amide) compound of example 2 | 31 | 409 | 319 | 842 |

COMPARATIVE EXAMPLE 1

300 g of xylenes were added to a 500 mL three-neck, round bottom flask. This flask was dropped into a 75° C. oil bath and an overhead stirring apparatus was attached. 150 mg (0.1 wt %) of DABCO catalyst and 75 g ethyl lactate were then added to this solution. Finally, 75 g of RUBINATE 44, from a 'melted out' stock supply in an 80° C. oven, was poured into an addition funnel connected to one of the flasks necks. A heat gun was used to prevent RUBINATE 44 recrystallization. The addition funnel's contents were then added drop wise over a 15-minute period. Attenuated Total Reflectance Fourier Transform Infrared Spectroscopy (from Thermo Fisher Scientific) was used to track the intensity reduction of the isocyanate peak, seen at approximately 2250 cm-1. Significant reduction was seen after 2.25 hours. At that point, the flask was removed from the oil bath and allowed to cool to room temperature. During this cooling, precipitation occurred resulting in the formation of a white solid. This could be promoted by placing the flask in an ice bath to further decrease the product's solubility in xylenes. The product was isolated by vacuum filtration over a three-day period.

Then, 13.8 g of JEFFAMINE D2000 and 11.1 g of JEFFAMINE D400 (from Huntsman) were poured into an 8 oz. jar making a 2:8 blend. The jar was then placed in a 100° C. oil bath and an overhead mixing apparatus was established. Afterwards, 0.41 mL tin octoate catalyst (a 1.25 wt % loading) was added to the blend. Finally, 16 g of the compound synthesized above (Rubinate 44/Ethyl Lactate adduct) was added. The (poly) urethane-amide compound was formed by stirring and heating the reactive mixture for a period of five hours.

Table 1 hereunder indicates the types of products used in the examples of the present invention.

TABLE 1

| CHEMICAL NAME | TRADE NAME | CAS | SUPPLIER | CHEMICAL STRUCTURE OF KEY COMPONENTS |
|---|---|---|---|---|
| DIPHENYLMETHANE 4,4'-DIISOCYANATE (4,4'MDI) | SUPRASEC ®1306 | 101-68-8 | HUNTSMAN | |
| POLY(PROPYLENE GLYCOL) (PPG 2000) MW 2000 G/MOL | ACCLAIM 2200 | 25322-69-4 | COVESTRO | |
| ETHYL LACTATE | ETHYL LACTATE | 687-47-8 | SIGMA-ALDRICH | |

TABLE 1-continued

| CHEMICAL NAME | TRADE NAME | CAS | SUPPLIER | CHEMICAL STRUCTURE OF KEY COMPONENTS |
|---|---|---|---|---|
| 1,4-DIAZABICYCLO [2.2.2]OCTANE | DABCO | 280-57-9 | SIGMA-ALDRICH | |
| POLYETHYLENEPOLYAMINE: CHAIN EXTENDER MOLECULAR WEIGHT MW BELOW 400 G/MOL (ABOUT 271 G/MOL) | ECA-29 | 68131-73-7 | HUNTSMAN | |

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

As used herein, the singular forms "a", "an", and "the" include both singular and plural referents unless the context clearly dictates otherwise. By way of example, "an isocyanate group" means one isocyanate group or more than one isocyanate group.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of". This means that, preferably, the aforementioned terms, such as "comprising", "comprises", "comprised of", "containing", "contains", "contained of", can be replaced by "consisting", "consisting of", "consists".

Throughout this application, the term "about" is used to indicate that a value includes the standard deviation of error for the device or method being employed to determine the value.

As used herein, the terms "% by weight", "wt %", "weight percentage", or "percentage by weight" are used interchangeably.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Throughout this application, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Although the preferred embodiments of the invention have been disclosed for illustrative purpose, those skilled in the art will appreciate that various modifications, additions or substitutions are possible, without departing from the scope and spirit of the invention as disclosed in the accompanying claims.

The invention claimed is:

1. A compound obtained by a process comprising the following steps:
   (i) Reacting at least one isocyanate containing compound, in stoichiometric excess, with at least one isocyanate-reactive compound having a number average molecular weight equal to or higher than 400, resulting in the formation of at least one prepolymer having soft blocks and hard blocks in its structure, which prepolymer contains unreacted isocyanate monomer,
   (ii) Reacting said at least one prepolymer with a hydroxyl-ester compound or a hydroxyl-acid compound to form a hydroxyl-ester terminated prepolymer or hydroxyl-acid terminated prepolymer, wherein the hydroxyl-ester terminated prepolymer contains hydroxyl-ester terminated monomer and the hydroxyl-acid terminated prepolymer contains hydroxyl-acid terminated monomer, and
   (iii) Ring-closing said hydroxyl-ester terminated prepolymer or hydroxyl-acid terminated prepolymer by processing said hydroxyl-ester terminated prepolymer or hydroxyl-acid terminated prepolymer in the presence of at least one catalyst to form a compound made of oxazolidinedione-terminated prepolymer and oxazolidinedione-terminated monomer, wherein the oxazolidinedione-terminated monomer is soluble in the oxazolidinedione-terminated prepolymer.

2. The compound according to claim 1, having a non-Newtonian viscosity.

3. The compound according to claim 1, wherein said at least one prepolymer of step (i) has a non-Newtonian viscosity.

4. The compound according to claim 1, wherein said at least one isocyanate containing compound and said at least one isocyanate-reactive compound are reacted at a molar ratio (NCO:OH) ranging from 1.05 to 15.

5. The compound according to claim 1, wherein said at least one prepolymer and said at least one hydroxyl-ester compound or said hydroxyl-acid compound are reacted at a molar ratio (NCO:OH) ranging from 0.5 to 1.2.

6. The compound according to claim 1, wherein said at least one prepolymer has an NCO value ranging from 0.8 to 10%, before performing step (ii).

7. The compound according to claim 1, wherein step (ii) is performed at a first temperature, resulting in the formation of said hydroxyl-ester terminated prepolymer or a hydroxyl-acid terminated prepolymer.

8. The compound according to claim 7, wherein step (ii) is carried out, at said first temperature, in a catalyst free condition.

9. The compound according to claim 7, wherein said ring-closure step is carried out at a second temperature.

10. The compound according to claim 9, wherein said catalyst is selected from the group consisting of 1,4-Diazabicyclo[2.2.2]octane (DABCO); 1,8-Diazabicyclo(5.4.0)undec-7-ene (DBU); Triazabicyclodecene (TBD); triethylamine; and potassium t-butanoate, or combination thereof.

11. The compound according to claim 1, wherein said hydroxyl-ester compound is selected from the group consisting of alpha-hydroxy ester compounds, beta-hydroxy ester compounds, hydroxyl containing esters derived from fatty acids, natural oils containing hydroxyl groups, or combinations thereof.

12. The compound according to claim 1, wherein said at least one prepolymer of step (i) has a hard block content ranging from 20 to 35 wt. %, based on the total weight of said at least one prepolymer.

13. The compound according to claim 1, having a hard block content ranging from 30 to 55 wt. %, based on the total weight of the compound.

14. A poly(urethane-amide) compound obtained by reacting a compound obtained according to claim 1, with at least one amine having a functionality of at least 1.8 and a hard block content ranging from at least 15% to 85%.

15. A product comprising poly(urethane-amide) compound according to claim 14.

* * * * *